United States Patent [19]

Bullard

[11] Patent Number: 5,381,787

[45] Date of Patent: Jan. 17, 1995

[54] EXTENDABLE AND RETRACTABLE LARYNGOSCOPE

[76] Inventor: James R. Bullard, P.O. Box 14727, Augusta, Ga. 30919-0727

[21] Appl. No.: 38,146

[22] Filed: Mar. 29, 1993

Related U.S. Application Data

[63] Continuation-in-part of Ser. No. 862,062, Apr. 2, 1992, which is a continuation-in-part of Ser. No. 780,445, Oct. 17, 1991, which is a continuation of Ser. No. 519,440, May 4, 1990.

[51] Int. Cl.$^6$ ................................................ A61B 1/26
[52] U.S. Cl. .................................... 128/11; 128/10; 128/4
[58] Field of Search .................. 128/11, 4, 6, 10, 20

[56] References Cited

U.S. PATENT DOCUMENTS

| | | | |
|---|---|---|---|
| 1,036,000 | 8/1912 | Pease . | |
| 3,266,059 | 8/1966 | Stelle . | |
| 3,749,088 | 7/1973 | Gauthier | 128/20 |
| 3,892,228 | 7/1975 | Mitsui . | |
| 4,337,761 | 7/1982 | Upsher . | |
| 4,360,008 | 11/1982 | Corazzelli, Jr. | 128/11 |
| 4,384,570 | 5/1983 | Roberts | 128/4 |
| 4,573,451 | 3/1986 | Bauman | 128/11 |
| 4,901,708 | 2/1990 | Lee | 128/11 |
| 4,947,829 | 8/1990 | Bullard | 128/11 |
| 5,036,835 | 8/1991 | Filli | 128/11 |
| 5,178,133 | 1/1993 | Pena | 606/198 X |

Primary Examiner—Stephen R. Crow
Assistant Examiner—Beverly A. Meindl
Attorney, Agent, or Firm—St. Onge Steward Johnston & Reens

[57] ABSTRACT

A laryngoscope with an extensible tip section is provided. The tip section extends from the blade and is remotely actuated to cause it to extend or retract as desired by the physician. The tip section is provided with alignment guides and retaining elements, and is lockable in the extended position. The laryngoscope permits remote manipulation of the blade to provide greater operational flexibility in using the laryngoscope.

14 Claims, 3 Drawing Sheets

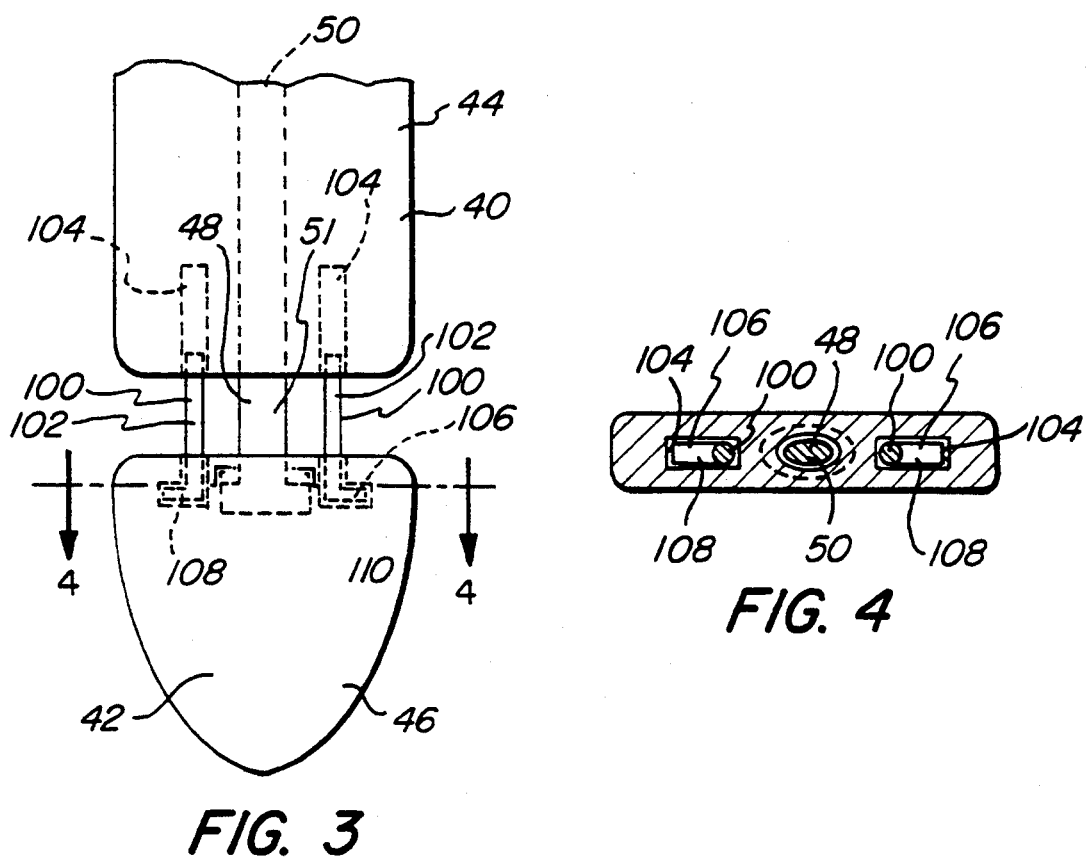
FIG. 3
FIG. 4
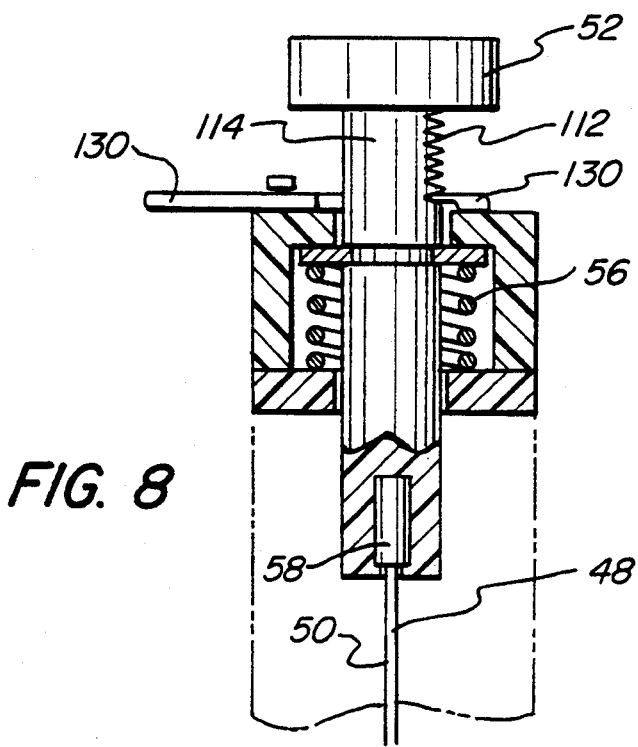
FIG. 8

EXTENDABLE AND RETRACTABLE LARYNGOSCOPE

This application is a continuation in part of copending U.S. patent application Ser. No. 07/862,062 filed Apr. 2, 1992 by the Applicant, James Roger Bullard, which is a continuation in part of copending U.S. patent application Ser. No. 07/780,445 filed Oct. 17, 1991 by the Applicant, James Roger Bullard, which is a continuation of U.S. patent application Ser. No. 07/519,440 filed May 4, 1990 by the Applicant, James Roger Bullard. This application is also a continuation in part of copending U.S. patent application Ser. No. 07/780,445 filed Oct. 17, 1991 by the Applicant, James Roger Bullard, which is a continuation of U.S. patent application Ser. No. 07/519,440 filed May 4, 1990 by the Applicant, James Roger Bullard.

FIELD OF THE INVENTION

The present invention relates to the field of medical optical devices permitting diagnosis and minimally invasive treatment and surgery, and more particularly, to an improved laryngoscope.

BACKGROUND OF THE INVENTION

Laryngoscopes are used in the medical field to facilitate endotracheal intubation of a patient during surgery to provide a positive air passageway for the administration of anesthesia and/or for the mechanical ventilation of the lungs of the patient. In the human anatomy, the epiglottis normally overlies the glottis opening into the larynx to prevent the passage of food into the trachea during eating; therefore, in endotracheal intubation, it is necessary to displace the epiglottis from the glottis opening to permit the endotracheal air tube to be inserted into the trachea.

A laryngoscope having means for indirect illumination and visualization of the pharyngeal areas of the body is disclosed in my U.S. Pat. No. 4,086,919, the disclosure of which is hereby incorporated by reference. U.S. Pat. No. 4,086,919 discloses a laryngoscope (hereafter the "Bullard laryngoscope") for endotracheal intubation which comprises a housing containing a working channel for containing forceps and channels containing fiber optics for lighting and viewing the internal areas of the body; and a laryngoscope blade for manipulating the epiglottis of a patient to enable viewing of a target area.

Various other laryngoscope constructions are known. Other prior art laryngoscopes have consisted of a metal blade which is supportably attached to a handle and is inserted through the mouth of the patient into the pharyngeal area to displace the tongue and epiglottis and permit direct visualization of the glottis opening through the mouth opening. Such laryngoscopes have been provided with a light source which is directed along the blade to illuminate the area beyond the distal end of the blade Two general types of rigid blade constructions are the straight, or so called "Miller blade", and the slightly curved, or so called "Macintosh blade". Curved laryngoscope blade constructions having light means to facilitate illumination of the areas of observation are described in U.S. Pat. Nos. 3,598,113; 3,643,654; 3,766,909; and 3,771,514.

A problem exists with the other prior art laryngoscopes in that in certain situations it is not possible to visualize and access a target area such as the glottis without substantial effort and distortion of the patient's internals. The Bullard laryngoscope resolves problems in the prior art by a laryngoscope design that is simple and effective in use.

The technique of intubation utilizing Bullard laryngoscopes is accomplished with a direct view of the larynx using either an intubating forcep or a styletted endotracheal tube. The oral introduction and placement of the Bullard laryngoscope in a patient is the same whether the intubating forcep or styletted endotracheal tube is used.

The blade of the Bullard laryngoscope is inserted into the oral cavity and the laryngoscope is rotated from the horizontal to the vertical position, allowing an anatomically shaped blade to slide around the tongue. Once the laryngoscope is fully vertical, final placement is facilitated by allowing the blade to drop momentarily to the posterior pharynx of the patient. The blade is then elevated against the tongue's dorsal surface. Only minimal upward movement exerted along the axis of the laryngoscope handle is required. This upward movement will result in the blade of the Bullard laryngoscope lifting the epiglottis, providing complete visualization of the glottis opening.

Prior to insertion of the Bullard laryngoscope into the patient, the user will have loaded an endotracheal air tube onto the laryngoscope by using the jaws of the intubating forceps in the working channel of the Bullard laryngoscope to grasp a Murphy eye in the endotracheal tube. The tube is brought to the patient's laryngeal entrance together with the laryngoscope by the above steps. Thereafter, the endotracheal tube is advanced by advancing the forceps towards the vocal cords until the tube is past the obstructions in the larynx. At this point the forceps are released from the endotracheal tube and the tube may be advanced in the airway to the extent necessary.

It has been found that the physical structure of the pharynx of different patients varies, and in particular, that the location of the glottis and epiglottis is not a consistent distance from the entry of the laryngoscope at the patient's mouth. Accordingly, in some patients it is necessary to remove the laryngoscope and mount a blade tip extender thereto, and then to reinsert the laryngescope. This removal and insertion is also necessary to change the laryngoscope blade if a modular blade laryngoscope is used. (A modular blade laryngoscope is disclosed in my U.S. Pat. No. 4,949,829, the disclosure of which is hereby incorporated by reference.) Eventually a laryngoscope with an effective blade length is obtained and the surgical procedure may continue.

It is to be appreciated that such multiple positioning and repositioning is time consuming and increases the risk of creating patient trauma and the cost of surgery. It would be desirable to minimize risk and cost by eliminating the iterative steps of determining the necessary size of a laryngoscope blade during the surgical operation.

SUMMARY OF THE INVENTION

It is an object of the invention to provide a laryngoscope with a remotely controlled blade end that is extendable and retractable, so that the blade length may be adjusted "in-situ", without requiring removal and subsequent re-establishment of the laryngoscope. It is an object of the invention to provide such a laryngoscope which has an atraumatic profile and which can provide effective manipulation of body structures.

These objects, and other objects as disclosed in this application, are achieved by a medical optical apparatus (such as a laryngoscope) having a body with a distal end and a proximal end. The body includes a working channel, and viewing and illuminating channels.

A rigid curved blade is affixed to the body. The blade extends generally beyond the body's distal end. An extensible and retractable blade tip section is provided at the distal end of the blade. The blade tip section is kept in alignment with the blade, preferably by alignment pins extending from the blade tip section into pin receiving bores in the blade The blade tip section is retained to the blade, preferably by stop elements on the alignment pins that prevent the pins from being withdrawn from the bores. The blade tip section is extendable by pressing on an actuator located at a proximate end of the laryngoscope body. The actuator is connected to the blade tip section by a cable that is sufficiently rigid to effectively cause the blade tip section to extend from the body. The blade tip section has a blunt, atraumatic profile, and, to avoid undesired pinching of the tissue between the blade and blade tip section, these portions are rounded, or else there is an elastic jacket joining these two portions of the laryngoscope blade. The actuator can be locked into position to keep the extended blade tip section in a selected position.

The apparatus of the invention permits controlled and selective extension and retraction of the blade to accommodate varying distances between the mouth and the epiglottis. This permits the use of a single size laryngoscope on a variety of patients and reduces the need to either position the laryngoscope awkwardly or to remove the installed laryngoscope and change the blade length when the blade is not effective in permitting visualization of the glottis opening. The present invention therefore provides a laryngoscope which provides substantial improvements in operational flexibility as compared with prior art devices.

Other objects, aspects and features of the present invention in addition to those mentioned above will be pointed out in detail or will be understood from the following detailed description provided in conjunction with the accompanying drawings.

BRIEF DESCRIPTION OF THE DRAWINGS

The foregoing aspects and other features of the invention are explained in the following description, taken in connection with the accompanying drawings, wherein:

FIG. 3 is a top plan view as in FIG. 2, with the blade tip section extended.

FIG. 4 is a cross-sectional view along the line 4—4 of FIG. 3 showing a laryngoscope blade tip section.

FIG. 8 is a view of an actuator for the blade tip section.

DETAILED DESCRIPTION OF THE INVENTION

Figure 2:
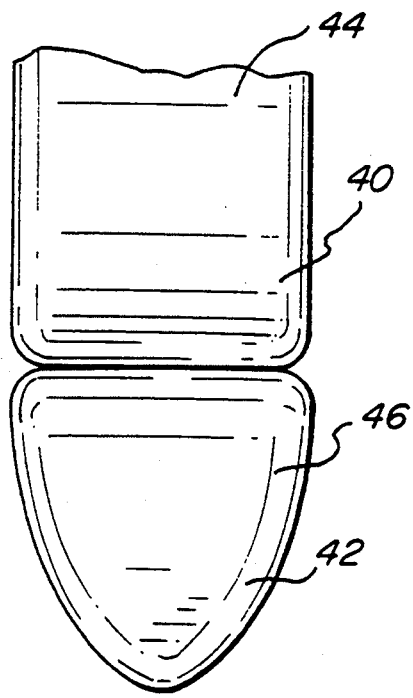
FIG. 2 is a top plan view of a detail of the blade and blade tip section of the laryngoscope of FIG. 1 with the blade tip section retracted.
Figure 1:
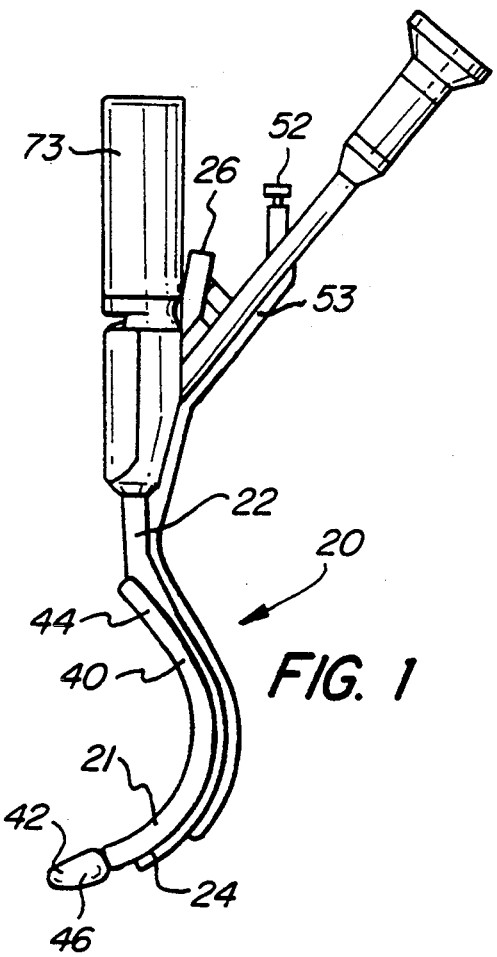
FIG. 1 is a perspective view of an extendable and retractable laryngoscope in accordance with one embodiment of the invention.

Referring to FIGS. 1-8, where like numbered elements in the drawings represent the same elements, a laryngoscope 20 is shown.

Laryngoscope 20 has a body 22, which is provided with a plurality of channels therein which extend from a distal end 24 to a proximal end 26 of the laryngoscope 20. Laryngoscope 20 is curved at its lower section 21 to generally conform with the curvature of the of human oral and pharyngeal passageways.

The blade 40 of the laryngoscope 20 generally comprises an elongate and rigid leaf. The blade 40 in this embodiment has a distal end 42 intended for insertion into the patient's mouth and a proximal end 44 connected to the body 22. Blade distal end 42 is controllably retractable and extendable by remote actuation. In particular, the blade distal end 42 comprises a blade tip section 46. Blade tip section 46 preferably has a blunt, atraumatic profile to reduce patient trauma during use of the laryngoscopes.

Tip section 46 is retained to blade 40 within its range of movement. Alignment guide or guides 100 are provided to maintain a consistent orientation of the blade tip section 46 with blade 40, and retainers 106 are provided to hold the blade tip section to the blade. In one preferred embodiment, guides 100 comprise alignment pins 102 extending from blade tip section 46 to fit into alignment pin receiving bores 104 provided in blade 40. In one preferred embodiment, the retainers 106 comprise stop elements 108 provided at ends 110 of alignment pins 102, and the pin receiving bores 104 have bore openings with a smaller diameter than the diameter of the step elements 108. Consequently, the tip section 46, while able to extend and retract, is prevented from separating from the blade 40.

The blade 40 in this embodiment preferably has an anatomically curved configuration (as does body 22) such that a physician can insert the blade 40 into the mouth of a patient while the patient is in a supine position. However, the invention is also usable in laryngoscopes with straight bodies and blades as are preferred in pediatric laryngoscopes.

The remote actuation of the distal end 42 of the blade tip section 46 of blade 40 may be achieved by providing an actuator, such as an axially extendable member 48 and an actuator button 52, which connect the blade tip section 46 and the blade 40. The axially extendable member 48 may comprise, for example, a stiff cable 50 extending through the body 22 (or a sleeve 53 along body 22) and blade 40. Actuator button 52 preferably comprises a spring returnable button 52 secured to cable 50. The cable 50 has sufficient rigidity so as not to collapse while pushing the blade tip section 46. In a preferred embodiment, cable 50 has a rigid extensible portion 51 adjacent the tip section 46, and the actuator button 52 is located adjacent a proximal end of body 22.

The remote control button is biased by a spring 56 and a connector 58 retains button 52 to cable 50. The spring 56 biases the button 52 in the outward position thus pulling on the cable 50. This in turn keeps the blade tip section 46 in its retracted position as shown in FIG.

Figure 5:
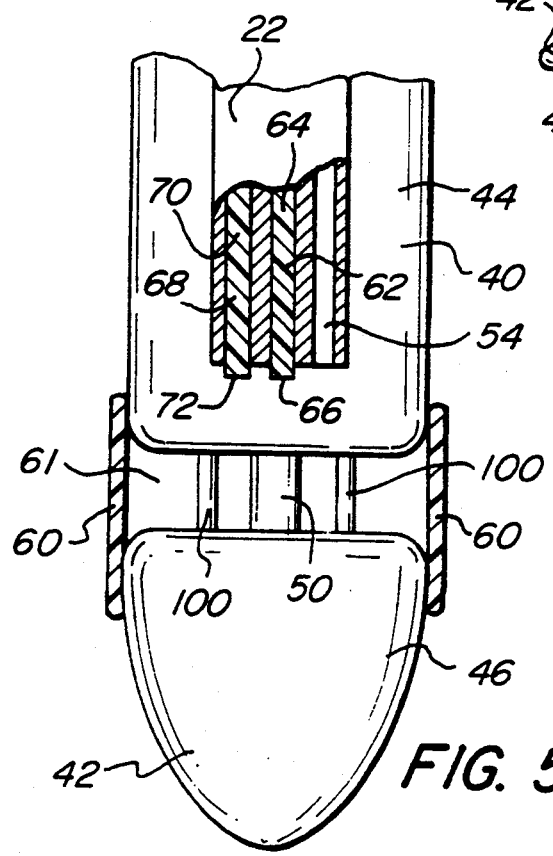
FIG. 5 is a bottom plan cutaway view of an alternative embodiment of the blade tip section of the laryngoscope of FIG. 1 in an extended position.

2. When the button 52 is depressed by an operator the cable 50 is pushed forward to extend the blade tip section 46, as shown in FIGS. 3 and 5. When the operator releases the button 52, the spring 56 pushes the button 52 back to its extended position. The button 52, in turn, pulls on the cable 50 which pulls on the blade tip section 46. This returns the blade tip section 46 back to its retracted position.

Means for locking the blade tip section 46 in an extended position are provided, and preferably comprise a lock mechanism such as latch 130 for locking in grooves 112 located in the shaft 114 of actuator button 52.

It is desirable to minimize trauma if the blade tip section 46 must be retracted in-situ by providing rounded edges between the tip section 46 and blade 40. Alternatively, as shown in FIG. 5, a resilient sheathing or jacket 60 is provided to cover or seal off the gap 61 between the extended blade tip section 46 and the blade end 64. The jacket 60 is preferably comprised of an elastic bio-compatible material. The jacket 60 prevents a patient's epiglottis or other structures from being pinched and traumatized by catching between the tip section 46 and blade 40.

At least one working channel 54 for forceps and other instruments will be provided in body 22. Other channels such as a suction and/or a washing spray channel may be provided in the body 22.

optical channel 62 is provided with a flexible optical image transmitting medium 64, which is preferably a bundle of optic fibers which extend from the distal end 24 to the proximal end 26 of the laryngoscope 20. The optical image transmitting medium 64 in the optical channel 62 permits optical images to be transmitted through the optical channel 62. The viewing lens 66 on the distal end of the optical channel 62 collects optical images for transmission through the optical channel 62. The laryngoscope 20 is preferably adapted so that a video camera may be operably coupled to the proximal end 26 of the laryngoscope 20 at the proximal end of the optical channel 62 to receive and transmit the optical images from the optical channel 62 to a television monitor (not shown) and to a video recording apparatus such as a video cassette recorder (not shown).

Light channel 68 is provided with the light transmitting medium 70 that permits light to be transmitted through the light channel 68. This permits the illumination of the field where treatment, diagnosis or operations are desired. The light transmitting medium 70 is preferably a plurality of optic fibers with another suitable lens 72 at the distal end thereof as necessary. The light transmitting medium 70 is connected at its proximal end to a light source of a sufficiently high intensity to permit visualization of the field. The light source may for example comprise a halogen bulb located in handle 73.

Figure 6:
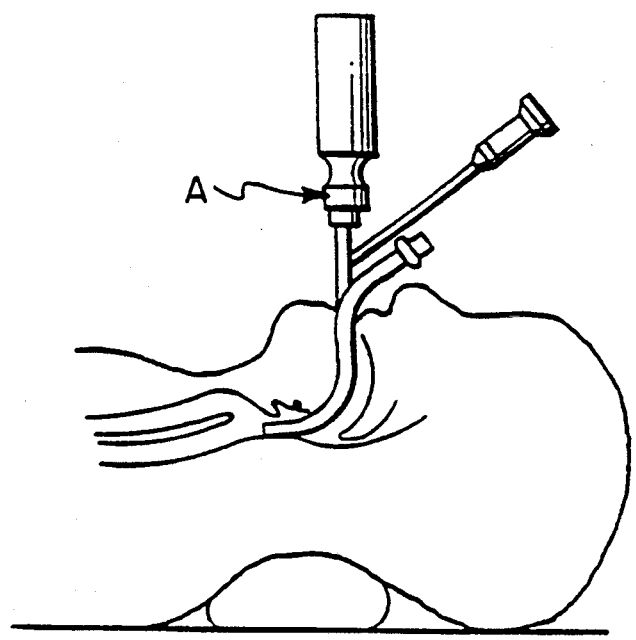
FIG. 6 is a view of a Bullard laryngoscope installed in a patient.

Referring to FIG. 6, there is shown an illustrated view of a patient in the supine position with a laryngoscope A, such as that disclosed in U.S. Pat. No. 4,905,669 to Bullard et al. inserted into the patient's mouth.

Although the laryngoscope shown in FIG. 6 is very effective, in certain circumstances, even with a curved blade, it is difficult to obtain access to a patient's glottal opening, requiring, for example, tilting or manipulation of the head to obtain access to the glottal opening. In certain circumstances, such as in the event of an upper spinal cord injury, tilting back a patient's head could be very dangerous to the patient. In addition, certain people such as children have such a small and recessed glottal opening that not even a curved blade can allow for fast intubation, even when the head is tilted back. It must also be emphasized that need for a fast intubation may be a life saving event such as in an emergency room situation.

Figure 7:
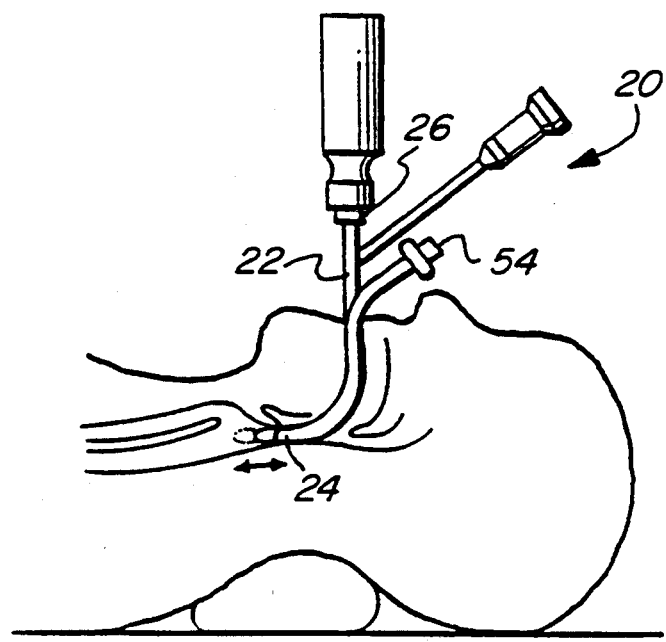
FIG. 7 is a view of a laryngoscope in accordance with one embodiment of the invention installed in a patient.

Referring now to FIG. 7, there is shown an illustrated view of a patient having a laryngoscope 20 incorporating features of the present invention positioned to place an intubation tube into the glottal opening of the patient. The present invention permits effective use of the laryngoscope in a variety of physical structures, by permitting the physician to adjust for differences between patient's anatomies.

The present invention provides an important and timely contribution to the art of medical devices, by providing a remotely controllable extension and retraction feature of the laryngoscope blade. This provides a laryngoscope that has better operational flexibility than any device known in the art.

It is to be appreciated that the foregoing is illustrative and not limiting of the invention, and that various changes and modifications to the preferred embodiments described above will be apparent to those skilled in the art. Such changes and modifications can be made without departing from the spirit and scope of the present invention, and it is therefore intended that such changes and modifications be covered by the following claims.

What is claimed is:

1. A laryngoscope comprising:
   a body having a working channel, and means for viewing and means for illuminating contained within said body;
   a rigid elongate curved blade for fitting into human oral and pharyngeal passageways, said curved blade being affixed to said body, said blade having a blade distal end having a blunt profile;
   said blade distal end being controllably extendable and retractable from said blade, said blade distal end including a blade tip section; alignment guides to maintain a consistent orientation of said blade tip section with said blade; retainers holding said blade tip section to said blade; and an actuator operably connected to said blade tip section for extending and retracting said blade tip section upon actuation thereof; said blade tip section having a proximal end having a cross-sectional shape which is generally similar to a cross-sectional shape of a distal end of said blade immediately adjacent said blade tip section proximal end, whereby said blade tip section when retracted joins with said blade to form a substantially consistent shape along the combined length of said blade and said blade tip section; and
   an elastic jacket having ends affixed to said blade and tip section, whereby a gap created upon extension of said tip section from said blade is covered by said jacket.

2. A laryngoscope in accordance with claim 1, wherein said actuator comprises an actuator button and a cable operably connecting said actuator button and said blade tip section.

3. A laryngoscope in accordance with claim 2, wherein said cable has a rigid extensible portion at a terminal portion thereof adjacent said blade tip section.

4. A laryngoscope in accordance with claim 2, wherein said actuator button is positioned at a proximal end of said body.

5. A laryngoscope in accordance with claim 2, wherein means for locking said blade tip section are provided to lock said blade tip section in a selected extended position.

6. A laryngoscope in accordance with claim 5, wherein said means for locking comprise a lock mechanism for said actuator.

7. A laryngoscope in accordance with claim 2, wherein said blade distal end extends generally beyond a distal end of said body.

8. A laryngoscope in accordance with claim 1, wherein said alignment guides comprise alignment pins extending from said blade tip section to fit into alignment pin receiving bores provided in said blade.

9. A laryngoscope in accordance with claim 8, wherein said retainers comprise stop elements provided at free ends of said alignment pins, and wherein said pin receiving bores have bore openings having a lesser diameter than a diameter of said stop elements.

10. A laryngoscope comprising:
a body having a working channel for containing a medical instrument, a fiber optic optical channel for viewing a target area, and a fiber optic illuminating channel for providing light to the target area;
a rigid elongate curved blade for fitting into human oral and pharyngeal passageways, said curved blade being affixed to said body, said blade having a blunt blade tip section at a blade distal end, said blade tip section being provided with an alignment guide to maintain a consistent orientation of said blade tip section with said blade and a retainer holding said blade tip section to said blade, said blade tip section having a proximal end having a cross-sectional shape which is generally similar to a cross-sectional shape of a distal end of said blade immediately adjacent said blade tip section proximal end, whereby said blade tip section when retracted joins with said blade to form a substantially consistent blunt shape along the combined length of said blade and said blade tip section;
an elastic jacket having ends affixed to said blade and blade tip section, whereby a gap created upon extension of said blade tip section from said blade is covered by said jacket;
an actuator mounted to said body and having an actuator button adjacent a proximal end of said body, said actuator button being operably connected to said blade tip section by a cable for controllably extending and retracting said blade tip section.

11. A laryngoscope in accordance with claim 10 wherein means for locking said blade tip section are provided to lock said blade tip section in a selected extended position.

12. A laryngoscope in accordance with claim 11, wherein said alignment guide comprises an alignment pin extending from said blade tip section to fit into an alignment pin receiving bore provided in said blade.

13. A laryngoscope in accordance with claim 12, wherein said retainer comprises stop elements provided at a free end of said alignment pin, and wherein said pin receiving bore has a bore opening having a lesser diameter than a diameter of said stop element.

14. A medical optical device comprising:
a body having a working channel for containing a medical instrument, a fiber optic optical channel for viewing a target area, and a fiber optic illuminating channel for providing light to the target area;
a rigid elongate working member, said working member being affixed to said body, said rigid elongate working member having a tip section at a distal end, said tip section being provided with an alignment guide to maintain a consistent orientation of said tip section with said working member and a retainer holding said tip section to said working member, said tip section having a proximal end having a cross-sectional shape which is generally similar to a cross-sectional shape of a distal end of said working member immediately adjacent said tip section proximal end, whereby said tip section joins with said working member to form a substantially consistent blunt shape along the combined length of said working member and said tip section;
an actuator operably connected to said tip section for controllably extending and retracting said tip section;
a protective sheathing having ends affixed to said working member and tip section, whereby a gap created upon extension of said tip section from said working member is enclosed by said sheathing; and
means for locking said tip section in a selected extended position.

* * * * *